US00PP29126P2

(12) United States Plant Patent
Dodd et al.

(10) Patent No.: US PP29,126 P2
(45) Date of Patent: Mar. 20, 2018

(54) APPLE TREE NAMED 'MAIA7'

(50) Latin Name: *Malus×domestica*
Varietal Denomination: MAIA7

(71) Applicants: William Dodd, Newcomerstown, OH (US); David Doud, Wabash, IN (US); John Mitchell Lynd, Pataskala, OH (US); Gregory Miller, Carrollton, OH (US)

(72) Inventors: William Dodd, Newcomerstown, OH (US); David Doud, Wabash, IN (US); John Mitchell Lynd, Pataskala, OH (US); Gregory Miller, Carrollton, OH (US)

( * ) Notice: Subject to any disclaimer, the term of this patent is extended or adjusted under 35 U.S.C. 154(b) by 0 days.

(21) Appl. No.: 15/330,372

(22) Filed: Sep. 12, 2016

(51) Int. Cl.
*A01H 5/08* (2006.01)

(52) U.S. Cl.
USPC ..... Plt./172

(58) Field of Classification Search
USPC ..... Plt./161, 172
CPC ..... A01H 5/0875
See application file for complete search history.

*Primary Examiner* — Kent L Bell

(57) ABSTRACT

A new and distinct variety of apple tree was identified from a population of seedlings derived from an open-pollinated 'Honeycrisp' progeny test. The new variety, named 'MAIA7' is distinct from 'Honeycrisp' as 'MAIA7' ripens mid-October, 4-5 weeks after 'Honeycrisp'. Unlike 'Honeycrisp', 'MAIA7' has yellow skin (R.H.S. Color Chart Yellow Group 13A), similar in appearance to 'Goldrush'. 'MAIA7' fruit are medium sized, extremely crisp, with complex sweet-tart flavors that includes tones of brown sugar and pineapple. 'MAIA7' maintains crisp texture and full flavor in 35° F. storage for at least 10 weeks longer than 'Honeycrisp'.

4 Drawing Sheets

Latin name of the genus and species of the plant claimed: *Malus×domestica.*

Variety denomination: 'MAIA7'.

BACKGROUND OF THE INVENTION

A new and distinct variety of apple tree was identified from a population of seedlings derived from an open-pollinated 'Honeycrisp' (U.S. Plant Pat. No. 7,197) block. This pollination was sanctioned as a part of the Midwest Apple Improvement Association apple breeding project. 'Honeycrisp' and other select varieties were cultivated with the intention of progeny testing open-pollinated seedlings. This superior seedling tree was identified from this progeny test at Pataskala, Ohio.

The seedling tree was planted as a 1-year-old tree at Pataskala, Ohio in 2001 and grown among a population of several hundred siblings. Evaluations of fruit quality and tree growth parameters were begun in 2005 and this seedling was identified over several years as superior based upon tree growth habit, precocity, superior fruit quality, and harvest time. Utilizing grafting reproduction, the new apple tree variety was asexually propagated by Mitch Lynd in 2010 at Pataskala, Ohio and has been observed to remain true to the description set forth herein. The closest comparison variety to 'MAIA7' is 'Golden Delicious'. 'MAIA7' differs from 'Golden Delicious' because of 'MAIA7's' flavor complexity that is tarter with fruity hints of pineapple and brown sugar. In addition, the apple size of 'MAIA7' is slightly smaller than 'Golden Delicious', typically ¼" diameter smaller under the same growing conditions.

The new variety, named 'MAIA7', is distinct from 'Honeycrisp' as 'MAIA7' ripens mid-October, 4-5 weeks after 'Honeycrisp' (FIG. 1) . Unlike 'Honeycrisp', 'MAIA7' has yellow skin (R.H.S. Color Chart Yellow Group 13A), similar in appearance to 'Goldrush' (U.S. Plant Pat. No. 9,392). 'MAIA7' fruit (FIGS. 2 & 3) are medium sized, extremely crisp, with complex sweet-tart flavors that includes tones of brown sugar and pineapple. 'MAIA7' maintains crisp texture and full flavor in 35° F. storage for at least 10 weeks longer than 'Honeycrisp' (FIG. 1).

BRIEF DESCRIPTION OF THE DRAWINGS

The accompanying photographs show typical specimens of the new variety depicted in color as true as is reasonably possible. 'MAIA7' photographs were taken in Pataskala, Ohio.

FIG. 1. Shows that 'MAIA7' is distinct from 'Honeycrisp' in both harvest time and storage window.

DETAILED BOTANICAL DESCRIPTION

Figure 1:
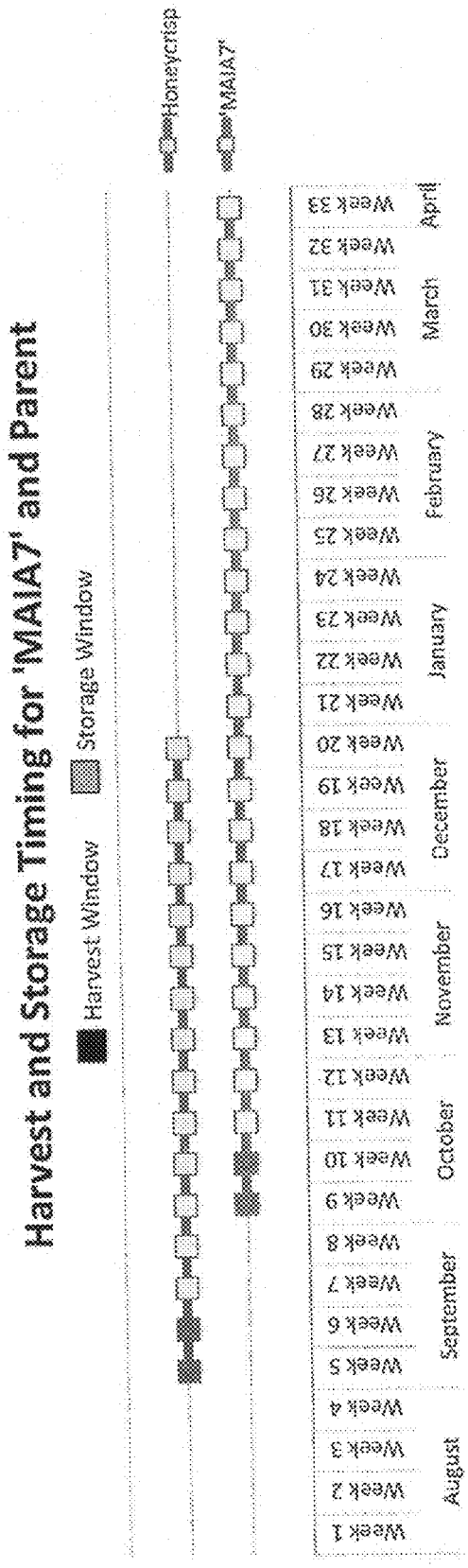
FIG. 1 was created from harvest data from Pataskala, Ohio, and storage data in Carrollton, Ohio.
Figure 2:
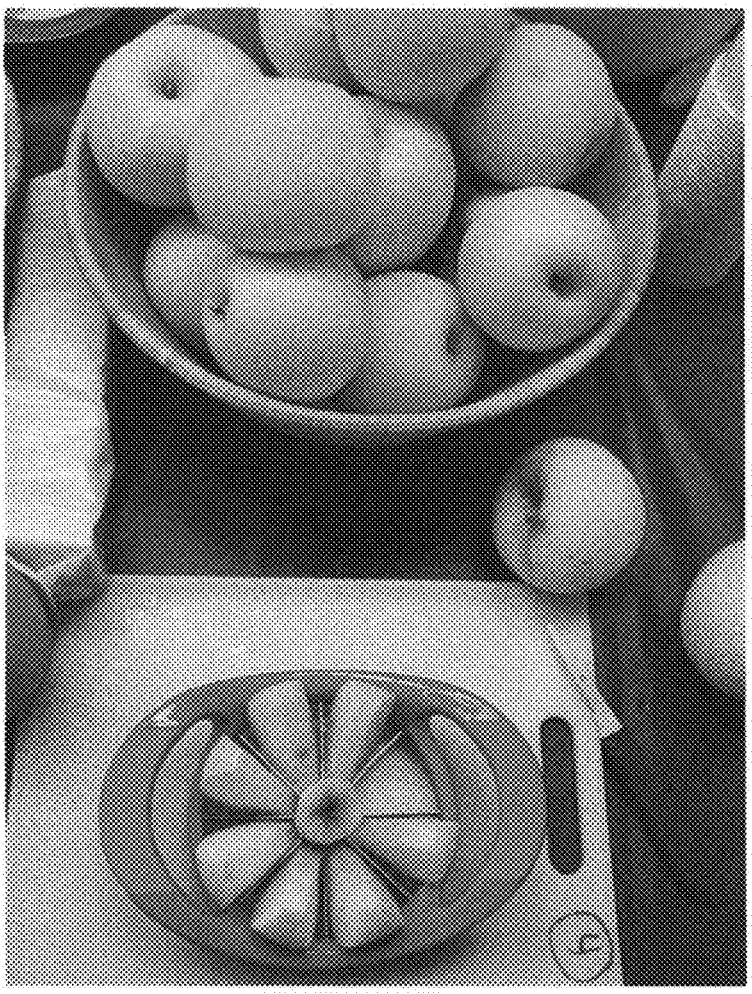
FIG. 2. Typical fruit of 'MAIA7' post-harvest.
Figure 3:
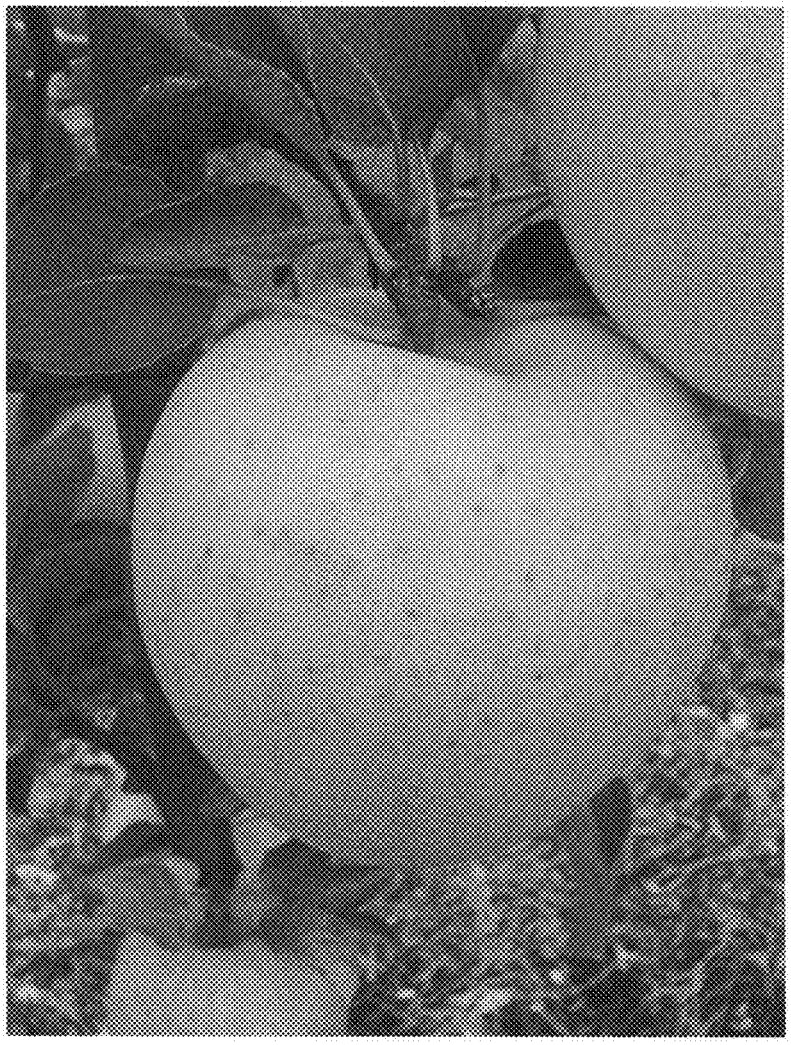
FIG. 3. Typical fruit of 'MAIA7' on the tree at harvest time.
Figure 4:
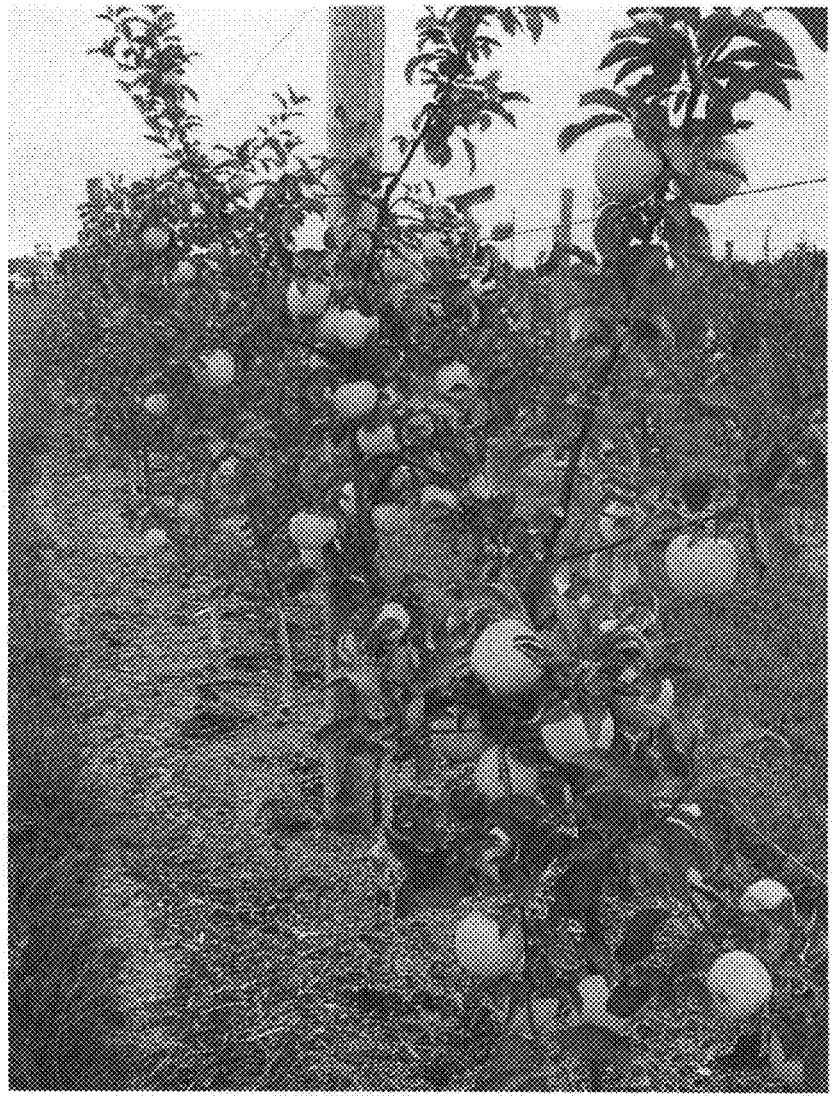
FIG. 4. Typical 'MAIA7' trees bearing fruit in October in Ohio.

Color references are made to The Royal Horticultural Society Color Chart (R.H.S.) 2001 Edition.

Parentage: 'Honeycrisp' female parent and unknown male parent; open pollination conditions cultivated by Mitch Lynd at Pataskala, Ohio in 1999.

Original seedling tree:

*Age.*—17 years.

*Size.*—Medium, 15' length, 15' spread.

*Vigor.*—Moderate.

*Form*.—Round, spreading.
*Production*.—Very productive.
*Growth type*.—Spindle tree growth form, productive spurs located throughout tree.
*Bearing*.—Annual.

Trunk:
*Original seedling tree size*.—13 cm at 15 cm height.
*Bark color*.—Brown Group 200C.
*Lenticel*.—Oblong, 3 mm×1 mm.
*Lenticel color*.—Grey-Brown Group N199D.
*Lenticel density*.—4 lenticels/cm$^2$.

Branches:
3 *year old*.—7-10 mm in diameter; typical branch length of 30-40 cm; branch angle 80-90°; color Greyed-Brown N199B.
2 *year old*.—5-6 mm in diameter; typical branch length of 23-30 cm; branch angle 80-90°; color Greyed-Brown N199B.
1 *year old*.—3-4 mm in diameter; typical branch length of 15-25 cm; branch angle 90°; color Greyed-Brown N199C.

Leaves:
*Size*.—Length 95 mm; width 45 mm.
*Texture*.—Leathery, crisp.
*Form*.—Ovate.
*Base*.—Roundly cuneate.
*Apex*.—Acute.
*Adaxial surface pubescence*.—None.
*Abaxial pubescence*.—Finely pubescent.
*Adaxial surface color*.—Green Group N137C.
*Abaxial surface color*.—Yellow-Green 147C.
*Veination*.—Pinnate, alternate, 8 major veins.
*Margin*.—Serrate.
*Petiole length*.—35 mm.
*Petiole width*.—3 mm.
*Petiole abaxial color*.—Yellow-Green 145C to Greyed-Purple 186A at base.
*Petiole adaxial surface color*.—Yellow-Green 145A to Greyed-Purple 187C toward base.
*Petiole groove*.—Present; depth 0.5 mm.
*Stipules*.—Present; 4 mm length; 1 mm width.
*Leaf glands*.—None observed.

Leaf buds:
*Length*.—3 mm.
*Width*.—2 mm.
*Shape*.—Both lateral and terminal buds pointed with imbricate scales.
*Color*.—Yellow-Green 145A with Greyed-Purple N186B overtones.
*Placement on branch*.—Alternate.
*Internode distance*.—35 mm.

Spurs:
*Length*.—Varies from 10 to 120 mm.
*Proportion*.—10-49 mm=14. 50-99 mm=5. 100-200=2.
*Width*.—5.2 mm.

Flowers at popcorn stage:
*Pedicel*.—Length 19-24 mm; diameter 1-2 mm.
*Pedicel color*.—Greyed-Green 197A.
*Bud*.—Length 9-11 mm; width 9-11 mm.
*Bud color*.—Red-Purple Group 63B to Red-Purple Group 69C.

Flowers at full bloom:
*Bloom time*.—Depends on spring temperatures, but with 'Golden Delicious'; typically during fourth week of April in northern Ohio.
*Bloom period*.—Variable with season; approximately 7 days.
*Presentation*.—Showy.
*Fragrance*.—Aromatic.
*Fertility*.—Fertile.
*Number of flowers per cluster*.—4-5 with 5 typical.

Petals:
*Arrangement*.—Bases not overlapping; 5 petals/flower; each petal 13-17 mm length and 8-10 mm width.
*Color*.—Upper surface (inside) Greyed-Green NN155D; lower surface (outside) Greyed-Green NN155D with Red-Purple 65C.
*Shape*.—Broadly ovate, abruptly cuneate at junction with receptacle.
*Veins*.—Distinct.
*Margins*.—Smooth edges with notching ⅔ the way up the petal on each side.
*Texture*.—Soft.
*Receptacle*.—Length 4-6 mm; width 3-4 mm; color Greyed-Green 197A with Greyed-Purple 186B
*Petal apex*.—Predominantly rounded with some fluting.
*Pedicel*.—Length 14-18 mm; width 1.5 mm; color Greyed-Green 197A.
*Sepals*.—5/flower; wedge-shaped; sharply pointed; length 8-11 mm; width 3 mm at widest point; adaxial and abaxial color Greyed-Green 197A.
*Stamens*.—18-20 in number.
*Anthers*.—Length 2-3 mm; width 2-3 mm; color Yellow 2D.
*Pollen*.—Present and abundant; color Yellow Group 10C.
*Filaments*.—Length 6-9 mm, increasing in length as flower matures; width 0.5 mm; color Greyed-Green 157D.
*Pistil*.—Held higher than anthers in majority of blossoms.
*Ovary*.—Length 4 mm; width 4 mm; color Green 143C.
*Style*.—Length 9-10 mm; styles are fused in bottom 3 cm only; color Greyed-Green 157B.
*Stigma*.—Width 0.5 mm; color Greyed-Green 193A.

Pollination requirements: Requires cross-pollination from diploid varieties with overlapping bloom; will pollinate diploid varieties of overlapping bloom.

Fruit:
*Maturity when described*.—5 week storage.
*Date of picking*.—Oct. 13, 2015.
*Size*.—Axial diameter 74-85 mm; transverse diameter 29-74 mm.
*Fruit weight*.—176-313 g, average 228 g.
*Form*.—Round ovate, sometimes oblique.
*Cavity*.—Acute medium deep, no russet in cavity, weak stem.
*Basin*.—Narrow width, abrupt, shallow, wavy asymmetrical.
*Calyx*.—Closed, reflexed.

Skin:
*Thickness*.—Thick.
*Tendency to crack*.—None.
*Lenticels*.—Triangular shape, increase in size from calyx end to stem end, 0-1 mm diameter.
*Stripes*.—None.
*Color*.—Yellow Group 13A with orange blush color (Yellow Orange 20A) on sun-exposed side of fruit.

*Ground color*.—Green-Yellow 1C.

Flesh:

*Aroma*.—Sweet, distinct apple.

*Locule number per fruit*.—5.

*Color*.—Yellow Group 4D.

*Texture*.—Crisp, firm, juicy.

*Eating quality*.—Excellent.

Core:

*Bundle area*.—964.8 $mm^2$.

*Bundle*.—Inconspicuous.

*Carpel axial length*.—9-11 mm.

*Seed cells*.—Walls thin, tough.

Seeds:

*Number perfect*.—3-12, average 7.

*Number in one cell*.—0-2.

*Length*.—7-8 mm.

*Breadth*.—4-5 mm.

*Color*.—Greyed-Orange 166D.

Stem:

*Length*.—21-32 mm.

*Width*.—2-3 mm.

*Color*.—Greyed-Yellow 160B.

Use: Fresh market, dessert.

*Fruit brix*.—15-18%.

*Yield*.—Approximately 2.5 bushel/tree at 300 trees/acre=750 bushels/acre annually.

Shipping quality: Good, subject to bruising.

Keeping quality: Excellent; 24 weeks in refrigerated storage.

Tree winter hardiness: Average for domestic apple.

Drought tolerance: Average for domestic apple.

Disease:

*Resistance*.—Resistant to apple scab (*Venturia inaequalis*); Resistant to fireblight (*Erwinia amylovora*).

*Susceptibility*.—Susceptible to powdery mildew (*Podoshaera leucotricha*) and other fungal diseases; fruit susceptible to soft rot (*Penicillium expansum*).

What is claimed is:

1. A new, distinct variety of apple tree named 'MAIA7', as illustrated and described herein.

* * * * *